(12) United States Patent
Chivukula et al.

(10) Patent No.: US 10,214,538 B2
(45) Date of Patent: Feb. 26, 2019

(54) PROCESS FOR PREPARATION OF DARUNAVIR

(71) Applicant: Laurus Labs Private Limited, Hyderabad (IN)

(72) Inventors: Kameswar R. Chivukula, Hyderabad (IN); Venkata R. Murthy, Hyderabad (IN); Venkata S. Indukuri, Hyderabad (IN); Seeta R. Gorantla, Hyderabad (IN)

(73) Assignee: Laurus Labs Ltd., Hyderabad (IN)

( * ) Notice: Subject to any disclaimer, the term of this patent is extended or adjusted under 35 U.S.C. 154(b) by 156 days.

(21) Appl. No.: 15/211,525

(22) Filed: Jul. 15, 2016

(65) Prior Publication Data

US 2016/0355525 A1    Dec. 8, 2016

Related U.S. Application Data

(62) Division of application No. 14/415,101, filed as application No. PCT/IB2013/001595 on Jul. 13, 2013, now Pat. No. 9,475,821.

(30) Foreign Application Priority Data

Jul. 24, 2012 (IN) .......................... 3021/CHE/2012

(51) Int. Cl.
  *C07D 493/04*    (2006.01)
  *C07C 303/38*    (2006.01)
(52) U.S. Cl.
  CPC .......... *C07D 493/04* (2013.01); *C07C 303/38* (2013.01); *C07B 2200/13* (2013.01)

(58) Field of Classification Search
  CPC .. C07D 493/04; C07C 303/38; C07B 2200/13
  See application file for complete search history.

(56) References Cited

U.S. PATENT DOCUMENTS

| 8,273,739 B2 | 9/2012 | De Pater |
| 9,175,005 B2* | 11/2015 | Parthasaradhi Reddy ................. C07D 307/93 |
| 2012/0035142 A1* | 2/2012 | Marom ................. A61K 31/34 514/158 |
| 2012/0251826 A1 | 10/2012 | Vellanki et al. |

FOREIGN PATENT DOCUMENTS

| CN | 1898248 A | 1/2007 |
| WO | WO-2011073993 A1 | 6/2011 |

OTHER PUBLICATIONS

CRC Handbook of Chemistry and Physics 2008 "Aqueous solubility and Henry's law Constants of Organic Compounds." CRC Handbook of Chemistry and Physics (2008): 5-154-5-189.

* cited by examiner

*Primary Examiner* — John M Mauro
(74) *Attorney, Agent, or Firm* — Blankrome LLP

(57) ABSTRACT

The present invention provides a process for the preparation of darunavir or solvates or a pharmaceutically acceptable salt thereof substantially free of bisfuranyl impurities, particularly darunavir propionate solvate. The present invention also provides a process for preparation amorphous darunavir using the darunavir propionate solvate.

8 Claims, 2 Drawing Sheets

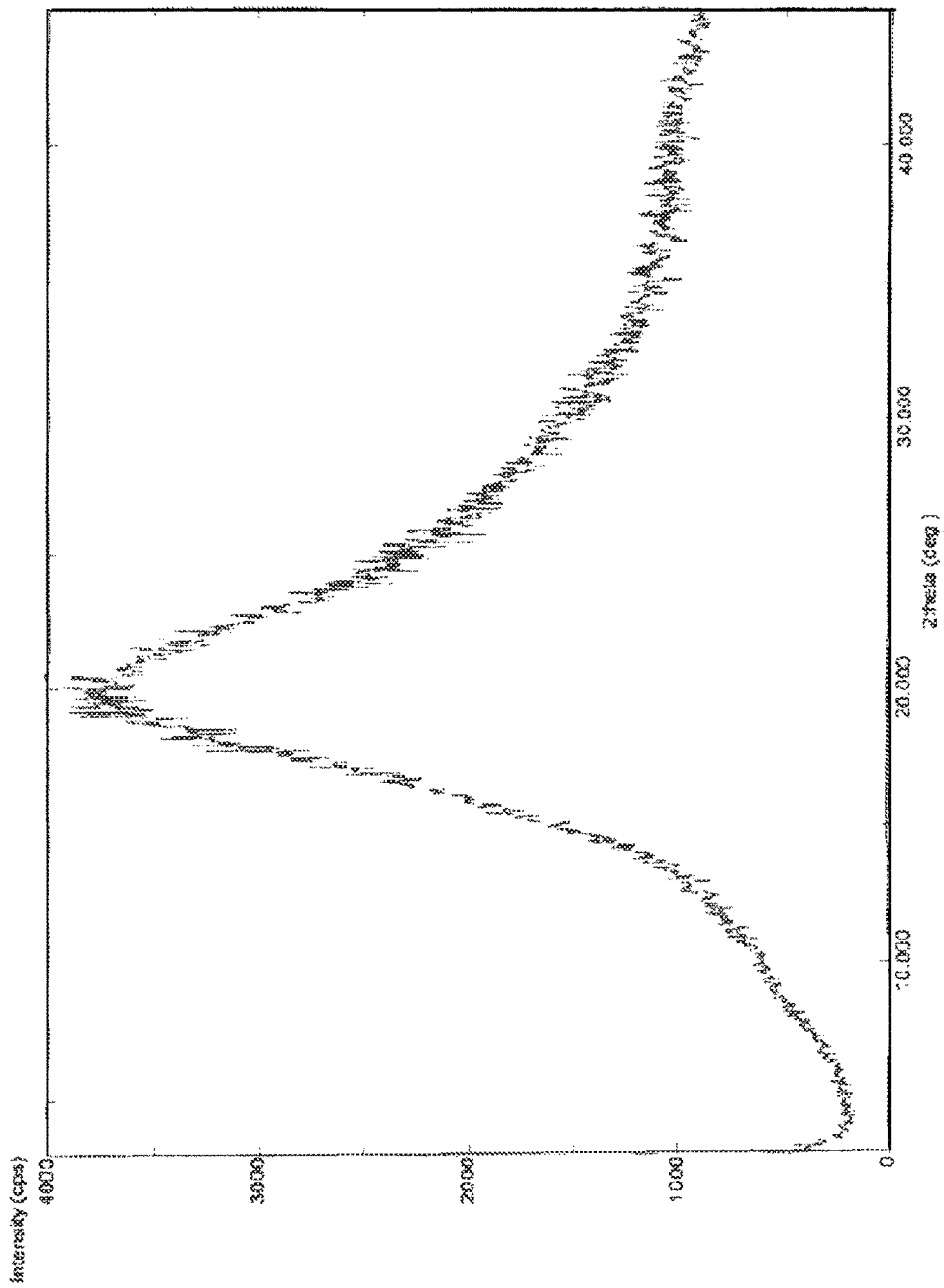

PROCESS FOR PREPARATION OF DARUNAVIR

CROSS REFERENCE TO RELATED APPLICATIONS

This application is a divisional of national stage U.S. patent application Ser. No. 14/415,101, filed on Jan. 15, 2015, which is based on and claims the benefit of International Application PCT/IB2013/001595, filed on Jul. 23, 2013, which is based on and claims the benefit of Indian Application No. 3021/CHE/2012, filed Jul. 24, 2012, the content of each of which is incorporated by reference herein.

FIELD OF THE INVENTION

The present invention generally relates to a process for preparation of Darunavir or solvates or a pharmaceutically acceptable salt thereof substantially free of bisfuranyl impurities and pharmaceutical compositions containing the same.

The present invention also relates to a process for preparation of amorphous Darunavir or a solvates or a pharmaceutically acceptable salt thereof and pharmaceutical compositions containing the same.

BACKGROUND OF THE INVENTION

Darunavir, also known as [(1S,2R)-3-[[(4-aminophenyl)sulfonyl](2-methylpropyl)amino]-2-hydroxy-1-(phenylmethyl)propyl]-carbamic acid (3R,3aS,6aR)-hexahydrofuro[2,3-b]furan-3-yl ester, is represented by the structural Formula I:

Formula I

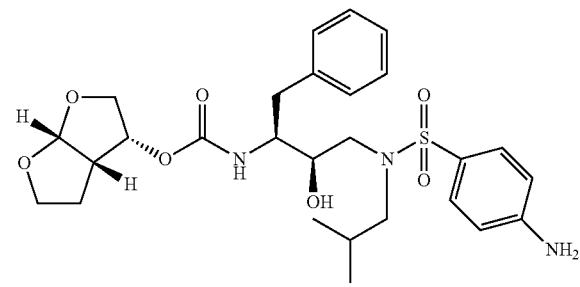

Darunavir is an inhibitor of the HIV protease belonging to the class of hydroxyethyl amino sulfonamides and is available as its ethanolate solvate under the name PREZISTA in the form of Eq75 mg, 150 mg, 400 mg and 600 mg base oral tablets and Eq100 mgbase/ml oral suspension.

Darunavir was first generically disclosed in U.S. Pat. No. 5,843,946 ("the 946 patent") and specifically disclosed in U.S. Pat. No. 6,248,775 ("the 775 patent"). The '775 patent further discloses a process for the preparation of darunavir active moiety, [(1S,2R)-3-[[(4-aminophenyl)sulfonyl](2-methylpropyl)amino]-2-hydroxy-1-(phenylmethyl)propyl]-carbamic acid of Formula II by reacting N-[3S-benzyloxycarbonylamino-2R-hydroxy-4-phenyl]-N-isobutylamine with 4-nitrobenzene sulfonyl chloride in presence of triethyl amine followed by hydrogenating the resultant nitro compound with palladium carbon. The '775 patent does not disclose any enabling disclosure for the preparation of darunavir (hexahydrofuranyl ester of Formula II). The process disclosed in the '775 patent is schematically represented as follows:

Formula II

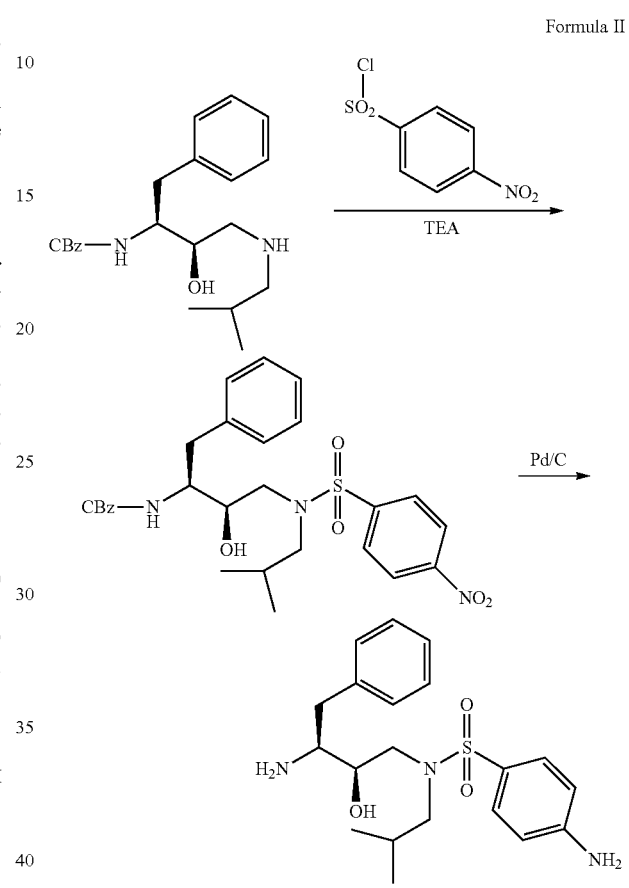

The '775 patent process involves simultaneous reduction of the nitro moiety and CBz deprotection in intermediate nitro compound results in a highly exothermic reaction that generates unwanted side reactions with the result that decreasing the product selectivity.

The first synthesis of darunavir was described in A. K. Ghosh et al. Bioorganic & Medicinal Chemistry Letters 8 (1998) 687-690, which is herein incorporated by reference. The synthesis includes reacting azido epoxide with isobutylamine and treatment of the resultant azido alcohol with p-nitrobenzene sulfonyl chloride to afford nitro compound. The nitro compound was hydrogenated with Palladium catalyst and then resultant amine compound was transformed to darunavir upon reaction with hexahydrofuro[2,3-b]furan-3-yl derivative in methylene chloride in the presence of 3 equivalents of triethylamine at 23° C. for 12 hours.

The process disclosed in the A. K. Ghosh et al is not suitable for large-scale production because it involves hazardous azide compounds; thus it requires utmost care to use. The process disclosed in the A. K. Ghosh et al is schematically represented as follows:

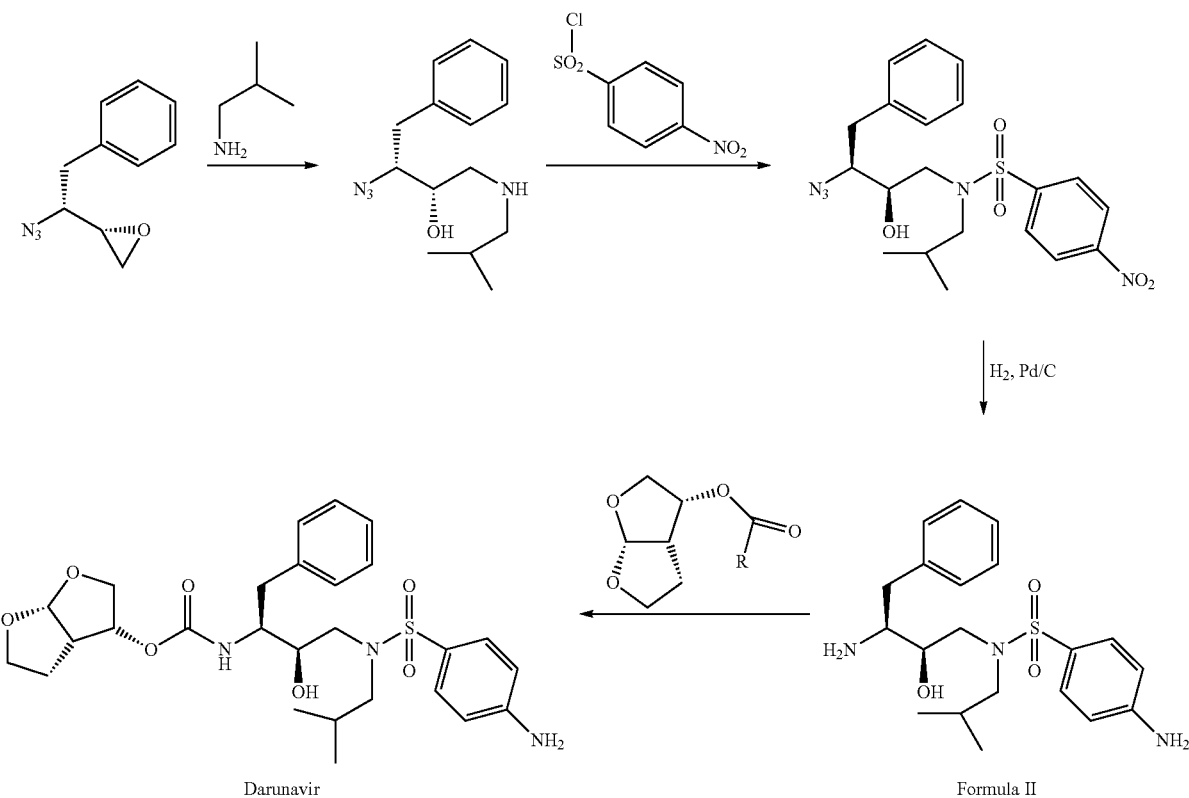

Darunavir

Formula II

To overcome the diffuculties associated with the A. K. Ghosh et al, alternate processes were disclosed, for example U.S. Pat. No. 7,772,411 ("the '411 patent") discloses the preparation of darunavir using boc-epoxide instead of azido epoxide as starting material. The '411 patent process involves a) reaction of boc epoxide with isobutylamine, b) introducing the p-nitrobenzene sulfonyl chloride c) reducing the nitro moiety d) deprotecting the boc protection and e) coupling the amine compound with hexahydrofuro [2,3-b] furan-3-yl derivative in a mixture of ethyl acetate and acetonitrile and in the presence of triethyl amine and methyl amine in aqueous ethanol.

Although the '411 patent process involves boc-epoxide instead of hazardous azido epoxide, the process still have difficulty to operate on large scale as it involves multistage synthesis hence the overall yield is limited to about 50%. The process disclosed in the '411 patent is schematically represented as follows:

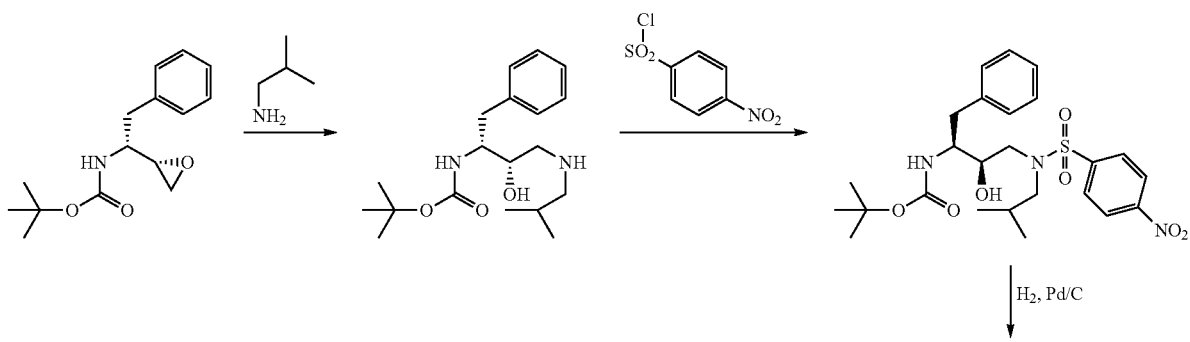

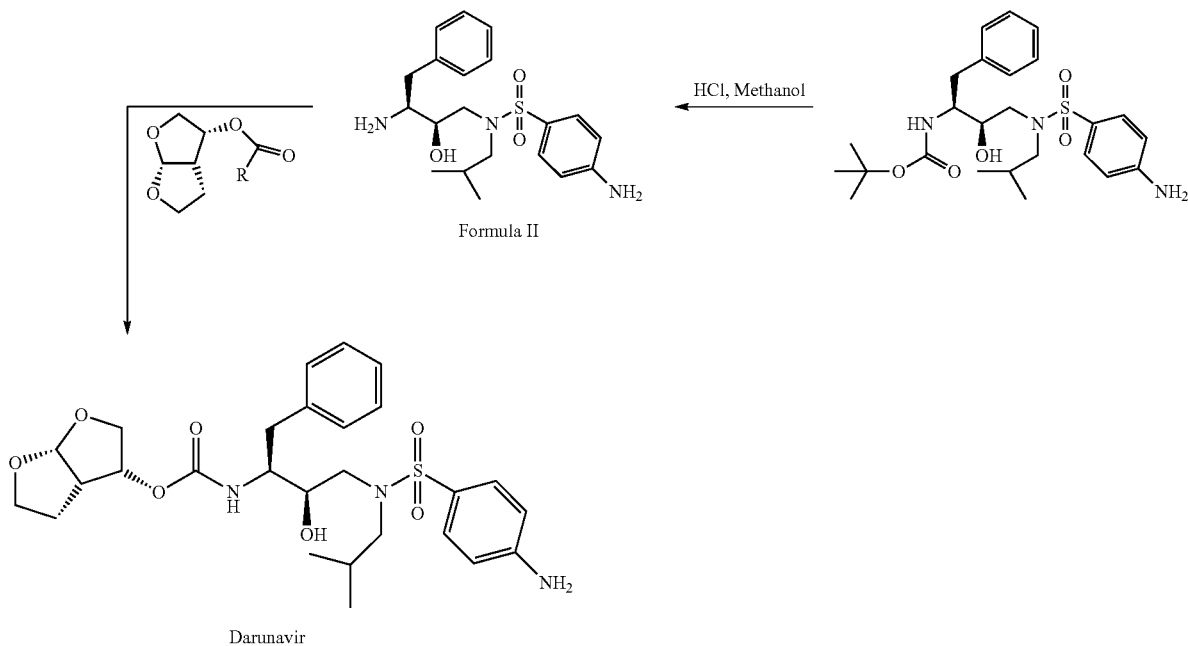

Formula II

Darunavir

PCT Publication No. WO 2010/023322 ("the '322 publication") discloses an alternate process of darunavir by a) reaction of boc-epoxide with N-benzyl-isobutylamine, b) deprotecting the amine protecting group c) coupling the amine compound with hexahydrofuro [2,3-b] furan-3-yl derivative d) removing the N-benzyl group e) introducing the p-nitrobenzene sulfonyl chloride and f) reducing the nitro moiety. The '322 publication process also involves multistep synthesis, this leads to an increase in the manufacturing cycle time. The process disclosed in the '322 publication process is schematically represented as follows:

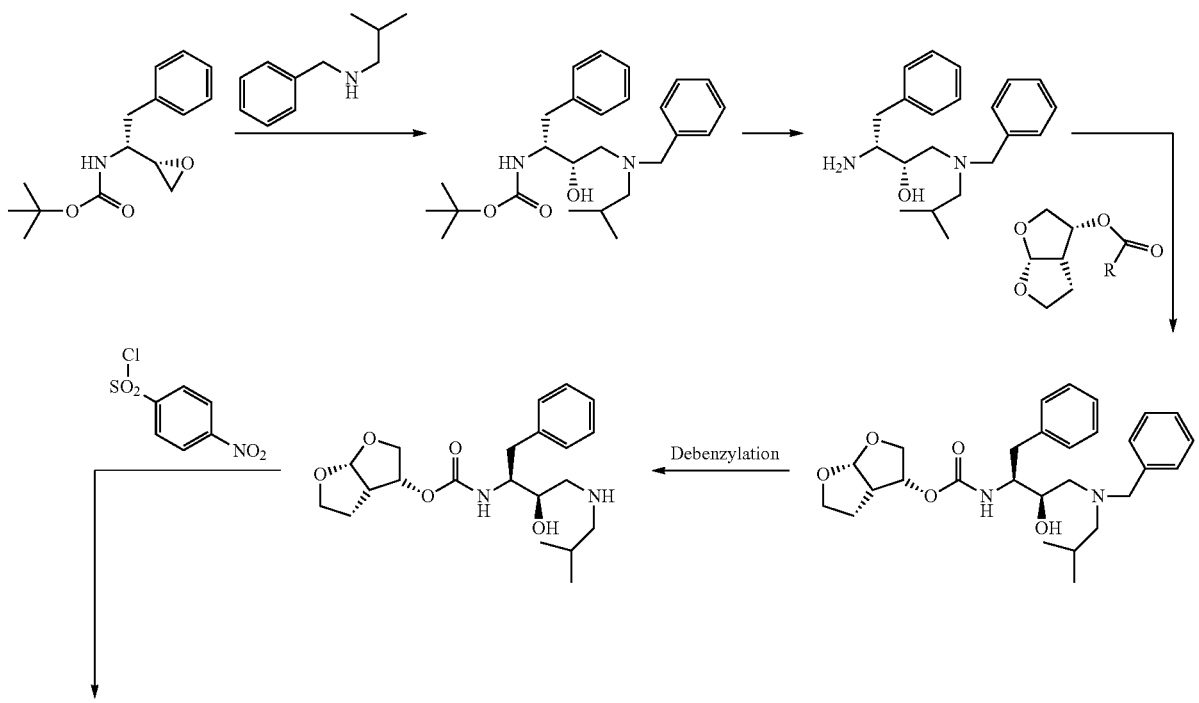

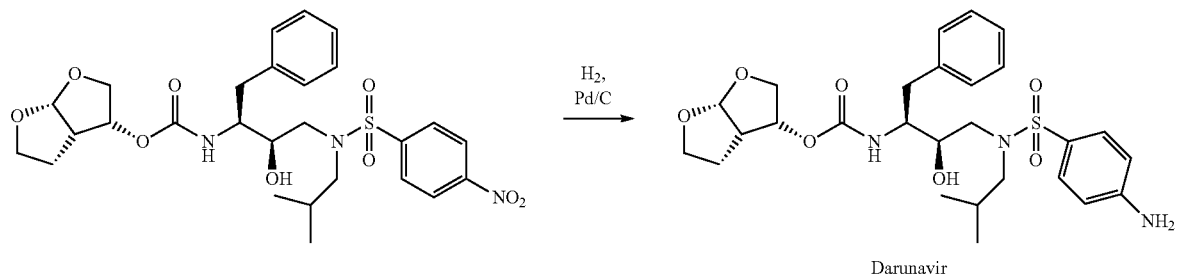

Darunavir

PCT Publication No. WO 2011/051978 ("the '978 publication") discloses an alternative process of darunavir by introducing furanyl compound before the nitro group reduction. This publication mention that the synthesis of darunavir by coupling of Formula II with hexahydrofuro [2,3-b] furan-3-yl derivative very likely leads to formation of impurities, viz., Impurity A and Impurity B.

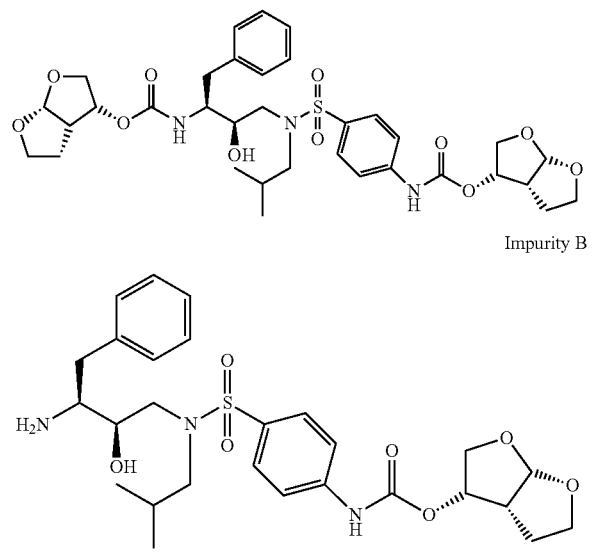

Impurity A

Impurity B

The process disclosed in the '978 publication process is schematically represented as follows:

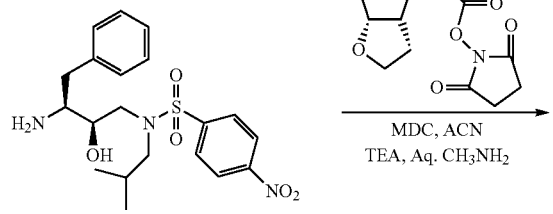

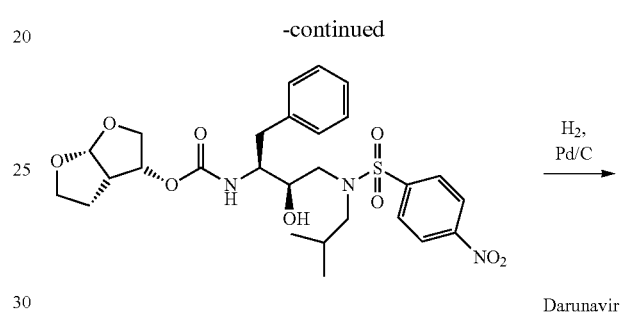

Darunavir

PCT Publication No. WO 2011/048604 ("the '604 publication") discloses a process for preparation of darunavir having bisfuranyl Impurity of Formula C less than 0.1% by coupling the 4-Amino-N-((2R,3S)-3-amino-2-hydroxy-4-phenyl)-N-(isobutyl)benzene sulfonamide with (3R,3aS,6aR)-hexahydrofuro[2,3-b]furan-3-ol derivative using N-methyl-2-pyrrolidinone as reaction solvent. The '604 publication further disclosed amorphous darunavir having particle size D50 of approximately 50 micrometers and D90 of approximately 100 to 180 micrometers.

Impurity C

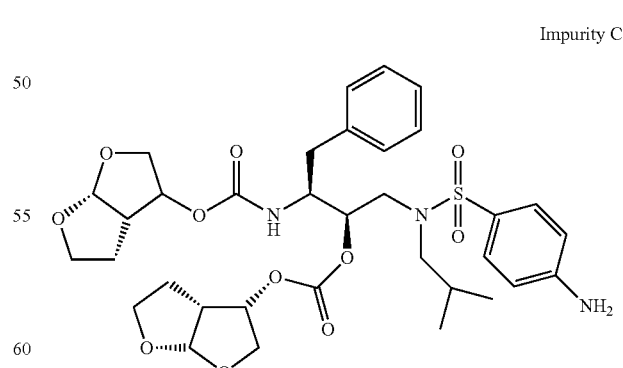

PCT Publication No. WO 2011/092687 ("the '687 publication") discloses a process for preparation of darunavir by following scheme:

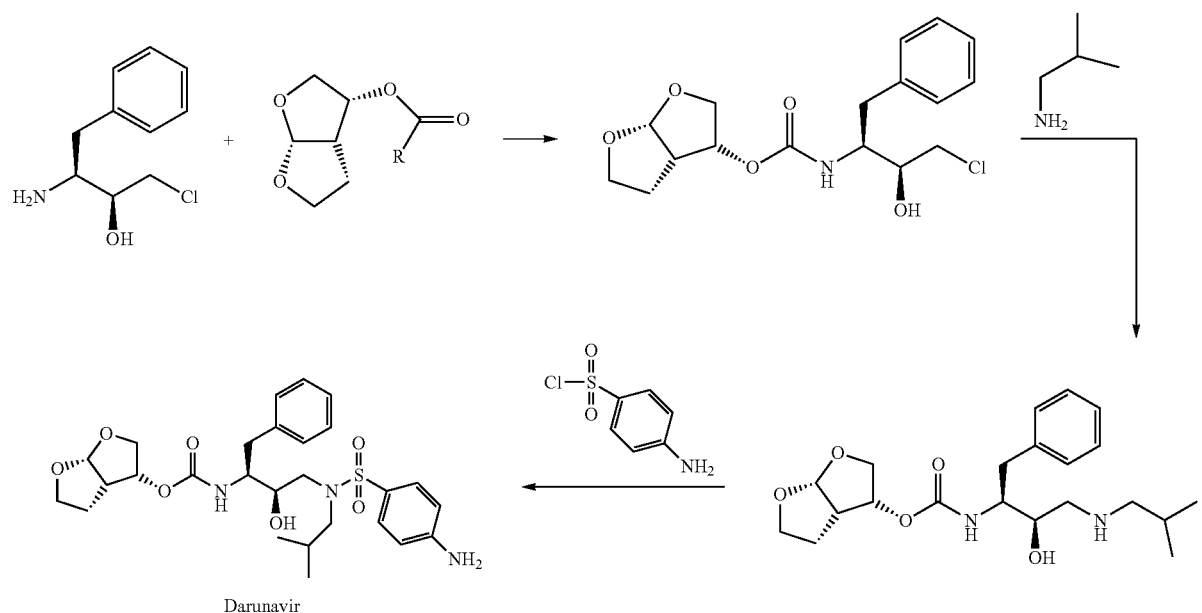

PCT Publication No. WO 2013/011485 ("the '485 publication") discloses a process preparation of darunavir by following scheme:

Several pseudopolymorphic forms of darunavir are described in the literature, for example U.S. Patent Application No. 2005/0250845 disclosed darunavir amorphous

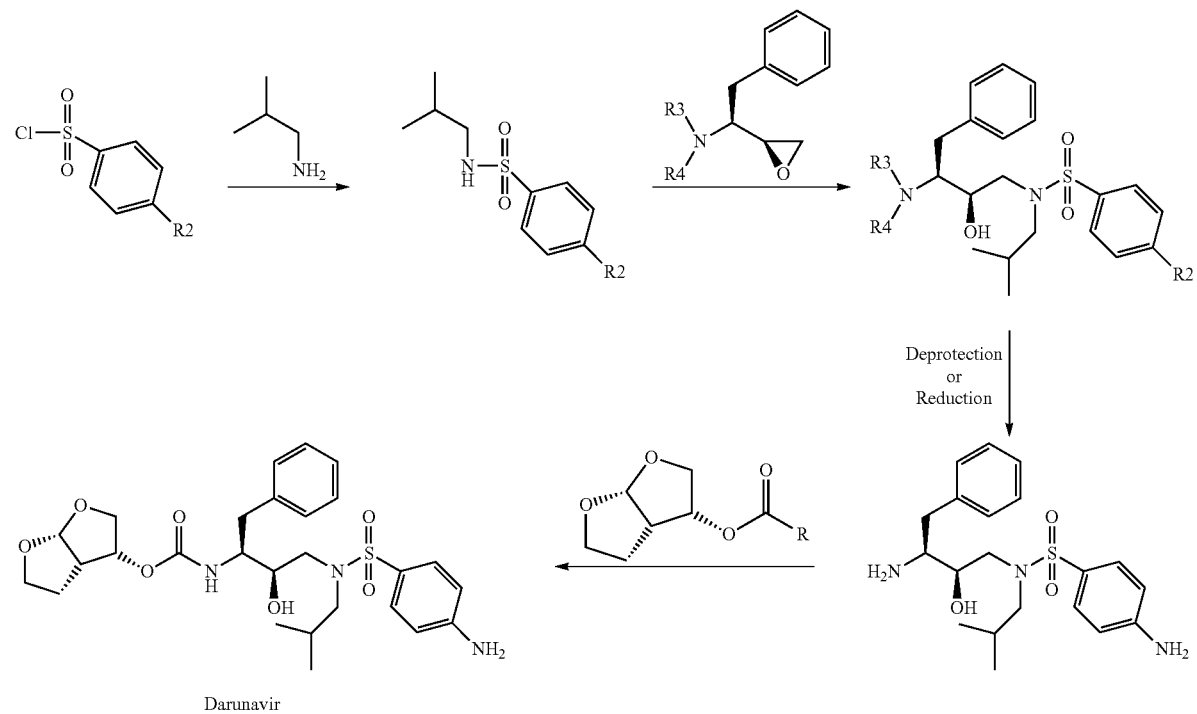

R2 is a NO2 or N(R4)2; R3 is an amino protecting group, R4 is hydrogen or an amino protecting group Darunavir can exist in different polymorphic forms, which differ from each other in terms of stability, physical properties, spectral data and methods of preparation.

Form, Form A (ethanolate), Form B (hydrate), Form C (methanolate), Form D (acetonate), Form E (dichloromethanate), Form F (ethylacetate solvate), Form G (1-ethoxy-2- propanolate), Form H (anisolate), Form I (tetrahydrofuranate), Form J (isopropanolate) and Form K (mesylate) of darunavir.

Journal of Molecular Biology, Vol 338, No 2, 23 Apr. 2004, pages 341-352 discloses the preparation of darunavir as white amorphous solid.

Amorphous Darunavir preparation was described in several ways in the literature, for example in WO2011/048604, WO2011/073993, WO 2011/083287, WO 2011/145099 & IN 2548/CHE/2009. Further WO2010/086844 describes the amorphous form of Darunavir with IR spectrum with characteristic peaks about 1454 and 1369 cm$^{-1}$.

The processes for preparation of darunavir described in the above literature have certain drawbacks as it involves: a) harsh reaction conditions for example nitro reduction using palladium carbon and hydrogen gas may lead to decomposition of sensitive carbamate linkage and further requires special pressure equipments for carrying out the synthesis, b) use of multiple solvents and bases during the introduction of furanyl ring makes the process not viable for large scale manufacturing.

Further darunavir obtained from the above processes was not satisfactory from purity point of view. Darunavir synthetic procedures as described in the art contained relatively large amounts of impurities, for example, when replicating the process of the '411 patent resulted in the elevation of bisfuranyl impurities. Extensive purification procedures are required in order to limit the impurities to less than the required as per regulatory guidelines; results low product yield thereby making the process quite expensive.

Hence there remains a need for an improved process to prepare darunavir, particularly amorphous form of darunavir, which is cost effective, industrially viable, and provide darunavir substantially free of impurities.

OBJECT OF THE INVENTION

The main object of the invention is to provide a simple, cost effective process for the preparation of darunavir with high purity and yield either without the formation or minimizing the formation of undesired impurities.

Another object of the invention is to provide a process for the preparation of darunavir wherein the process excludes the use of multiple solvents and multiple bases instead of use simple water immiscible organic solvent and water without use of any base during the reaction of amine compound of Formula II and (3R,3aS,6aR)-hexahydrofuro[2,3-b]furan-3-ol derivative, thereby minimizing the formation of bisfuranyl impurities, making the process more suitable for commercial applications.

Yet another object of the invention is to provide a process for the preparation of darunavir wherein the process excludes the use of nitro compounds thereby avoiding harsh nitro reductions using palladium with hydrogen gas, making the process more convenient and safe to use on an industrial scale.

SUMMARY OF THE INVENTION

The present invention encompasses a process for the preparation of darunavir or solvates or a pharmaceutically acceptable salt thereof with high product yield and quality, particularly darunavir in amorphous form substantially free of bisfuranyl impurities.

In accordance with one embodiment, the present invention provides a process for preparation of darunavir of Formula I or solvates or a pharmaceutically acceptable salt thereof, Formula I comprising:
a) reacting 4-amino-N-(2R, 3S) (3-amino-2-hydroxy-4-phenylbutyl)-N-isobutyl-benzenesulfonamide of Formula II Formula II with (3R, 3aS, 6aR)-hexahydrofuro [2,3-b]furan-3-ol derivative in a mixture of water immiscible organic solvent and water, and
b) isolating darunavir.

In accordance with a second embodiment, the present invention provides a process for preparation of darunavir, comprising:
a) reacting 4-amino-N-(2R, 3S) (3-amino-2-hydroxy-4-phenylbutyl)-N-isobutyl-benzenesulfonamide of Formula II with (3R, 3aS, 6aR)-hexahydrofuro [2,3-b] furan-3-ol derivative in a mixture of water immiscible organic solvent and water, and
b) isolating darunavir;
wherein the water immiscible organic solvent is selected from the group consisting of esters, ethers, halogenated hydrocarbons, aromatic hydrocarbons and the like.

In accordance with a third embodiment, the present invention provides a process for preparation of darunavir, comprising:
a) reacting 4-amino-N-(2R, 3S) (3-amino-2-hydroxy-4-phenylbutyl)-N-isobutyl-benzenesulfonamide of Formula II with (3R, 3aS, 6aR)-hexahydrofuro [2,3-b] furan-3-ol derivative in a mixture of water immiscible organic solvent and water, and
b) crystallizing darunavir from a carboxylic acid solvent, and
c) isolating the darunavir.

In accordance with a fourth embodiment, the present invention provides a process for preparation of darunavir, comprising:
a) reacting 4-amino-N-(2R, 3S) (3-amino-2-hydroxy-4-phenylbutyl)-N-isobutyl-benzenesulfonamide of Formula II with (3R, 3aS, 6aR)-hexahydrofuro [2,3-b] furan-3-ol derivative in a mixture of water immiscible organic solvent and water, and
b) crystallizing darunavir from a carboxylic acid solvent,
c) isolating the corresponding darunavir carboxylic acid solvate, and
d) converting the darunavir carboxylic acid solvate in to darunavir.

In accordance with a fifth embodiment, the present invention provides a process for preparation of darunavir, comprising:
a) reacting 4-amino-N-(2R, 3S) (3-amino-2-hydroxy-4-phenylbutyl)-N-isobutyl-benzenesulfonamide of Formula II with (3R, 3aS, 6aR)-hexahydrofuro [2,3-b] furan-3-ol derivative in a mixture of water immiscible organic solvent and water, and
b) crystallizing darunavir in propionic acid,
c) isolating the darunavir propionate solvate, and
d) converting the darunavir propionate solvate in to darunavir.

In accordance with a sixth embodiment, the present invention provides darunavir propionate solvate.

In accordance with a seventh embodiment, the present invention provides darunavir propionate characterized by an X-Ray diffraction (XRD) pattern substantially in accordance with FIG. 1.

In accordance with an eighth embodiment, the present invention provides a process for preparation of 4-amino-N-(2R, 3S) (3-amino-2-hydroxy-4-phenylbutyl)-N-isobutyl-benzenesulfonamide of Formula II,

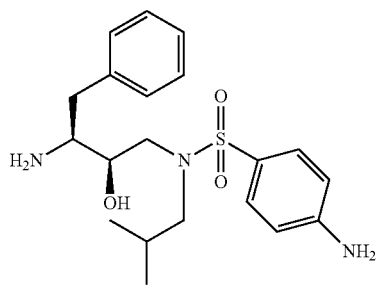

Formula II comprising:
a) reacting a compound of Formula IV

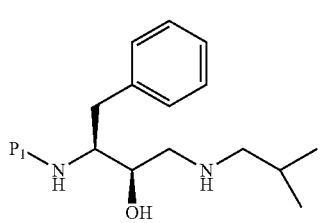

Formula IV wherein 'P$_1$' represents hydrogen or a suitable amine protecting group selected from the group consisting of acetyl, tertiary butyloxy carbonyl (Boc), p-nitrobenzoyl (PNB), p-methoxybenzoyl (PMB), trityl and the like, with a protected benzene sulfonyl chloride of Formula IV'

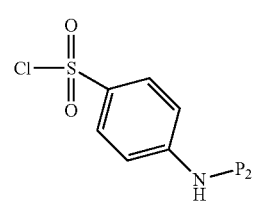

Formula IV' wherein 'P$_2$' represents hydrogen or a suitable amine protecting group selected from the group consisting of acetyl, tertiary butyloxy carbonyl (Boc), p-nitrobenzoyl (PNB), p-methoxybenzoyl (PMB), trityl and the like; to obtain a compound of Formula III

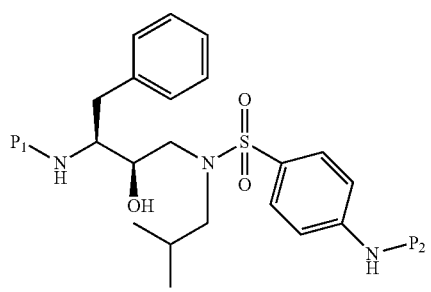

Formula III wherein 'P$_1$' and 'P$_2$' represents hydrogen or a suitable amine protecting group, and
a) deprotecting the resultant compound with a suitable deprotecting medium.

In accordance with a ninth embodiment, the present invention provides a process for preparation of darunavir of Formula I or solvates or a pharmaceutically acceptable salt thereof,

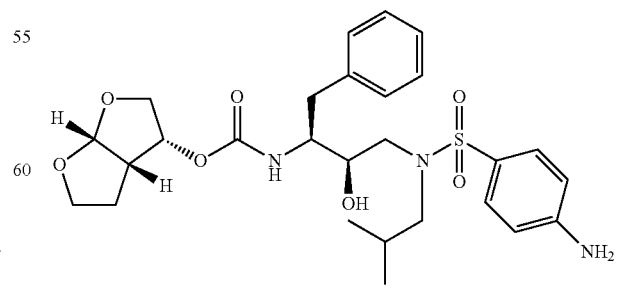

Formula I comprising:
a) reacting a compound of Formula IV

Formula IV

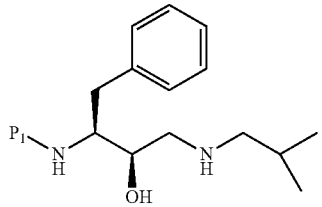

wherein 'P₁' represents hydrogen or a suitable amine protecting group selected from the group consisting of acetyl, tertiary butyloxy carbonyl (Boc), p-nitrobenzoyl (PNB), p-methoxybenzoyl (PMB), trityl and the like, with a protected benzene sulfonyl chloride of Formula IV'

Formula IV'

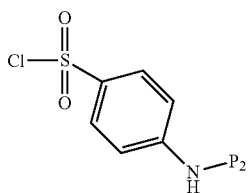

wherein 'P₂' represents hydrogen or a suitable amine protecting group selected from the group consisting of acetyl, tertiary butyloxy carbonyl (Boc), p-nitrobenzoyl (PNB), p-methoxybenzoyl (PMB), trityl and the like; to obtain a compound of Formula III Formula III

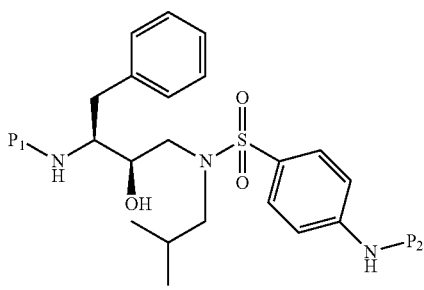

wherein 'P₁' and 'P₂' represents hydrogen or a suitable amine protecting group selected from the group consisting of acetyl, tertiary butyloxy carbonyl (Boc), p-nitrobenzoyl (PNB), p-methoxybenzoyl (PMB), trityl and the like, a) deprotecting the resultant compound with a suitable deprotecting medium to obtain a compound of Formula II, Formula II

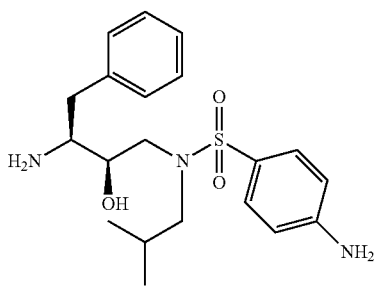

b) reacting the resultant compound of Formula II with (3R, 3aS, 6aR)-hexahydrofuro [2,3-b]furan-3-ol derivative in a mixture of water immiscible organic solvent and water,
c) crystallizing darunavir in carboxylic acid,
d) isolating the darunavir carboxylic acid solvate, and
e) converting the darunavir carboxylic acid solvate in to darunavir.

In accordance with a tenth embodiment, the present invention provides a process for preparation of darunavir of Formula I or solvates or a pharmaceutically acceptable salt thereof, Formula I

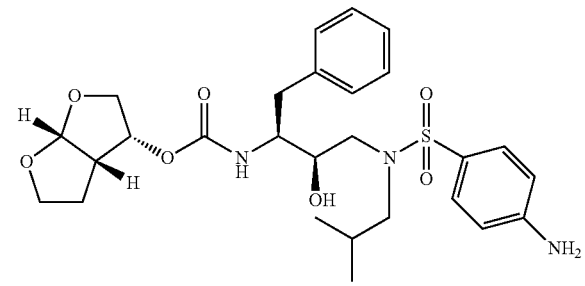

comprising:
a) reacting (1-benzyl-2-hydroxy-3-isobutylaminopropyl) carbamic acid tertiary butyl ester of Formula

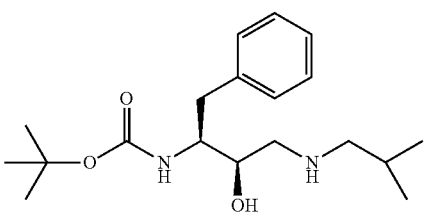 [SMILES: CC(C)CNC[C@@H](O)[C@H](Cc1ccccc1)NC(=O)OC(C)(C)C]

with a N-acetyl benzene sulfonyl chloride of Formula

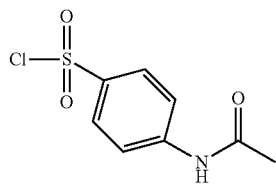

to obtain a compound of Formula III

Formula III

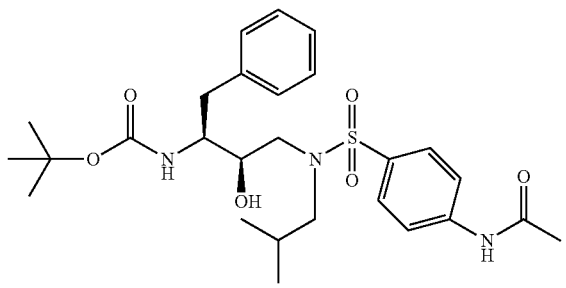

a) deprotecting the resultant compound with an acid to obtain 4-amino-N-(2R, 3S) (3-amino-2-hydroxy-4-phenylbutyl)-N-isobutyl-benzenesulfonamide of Formula II, Formula II

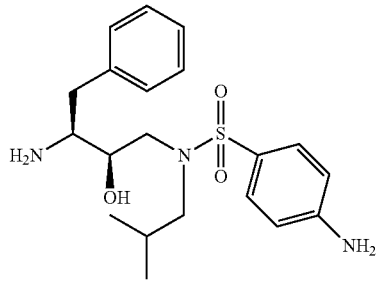

b) reacting the resultant compound of Formula II with (3R, 3aS, 6aR)-hexahydrofuro [2,3-b]furan-3-ol derivative in a mixture of water immiscible organic solvent and water,
c) crystallizing darunavir in carboxylic acid,
d) isolating the darunavir carboxylic acid solvate, and
e) converting the darunavir carboxylic acid solvate in to darunavir.

In accordance with an eleventh embodiment, the present invention provides a process for preparation of amorphous darunavir, comprising the steps of:
a) providing a solution of darunavir in any form or obtained by the processes herein described above in an acid and water,
b) combining step a) solution and a solution of a base and water,
c) recovering amorphous darunavir.

In accordance with a twelfth embodiment, the present invention provides a process for preparation of amorphous darunavir, comprising the steps of:

a) providing a solution of darunavir or solvates or a pharmaceutically acceptable salt thereof, obtained by the processes herein described above in an acid and a solvent optionally a base,
b) combining step a) solution and a solution of a base and water,
c) recovering amorphous darunavir.

In accordance with a thirteenth embodiment, the present invention provides a process for preparation of amorphous darunavir, comprising the steps of:
a) providing a solution of darunavir or solvates or a pharmaceutically acceptable salt thereof, obtained by the processes herein described above in an acid and a solvent optionally a base,
b) combining step a) solution and a solution of a base and water,
c) recovering amorphous darunavir;
wherein the acid is an organic acid, the solvent is selected from the group comprising nitriles, alcohols, water and the like and the base in an inorganic base.

In accordance with a fourteenth embodiment, the present invention provides a process for preparation of amorphous darunavir, comprising the steps of:
a) providing a solution of darunavir propionate solvate in acetic acid, acetonitrile and ammonia,
b) combining step a) solution and a solution of a ammonia and water,
c) recovering amorphous darunavir.

In accordance with a fifteenth embodiment, the present invention provides pharmaceutical composition comprising darunavir or solvates or a pharmaceutically acceptable salt thereof prepared by the processes of the present invention and at least one pharmaceutically acceptable excipient.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 2 is the characteristic powder X-ray diffraction (XRD) pattern of amorphous darunavir.

DETAILED DESCRIPTION OF THE INVENTION

Figure 1:
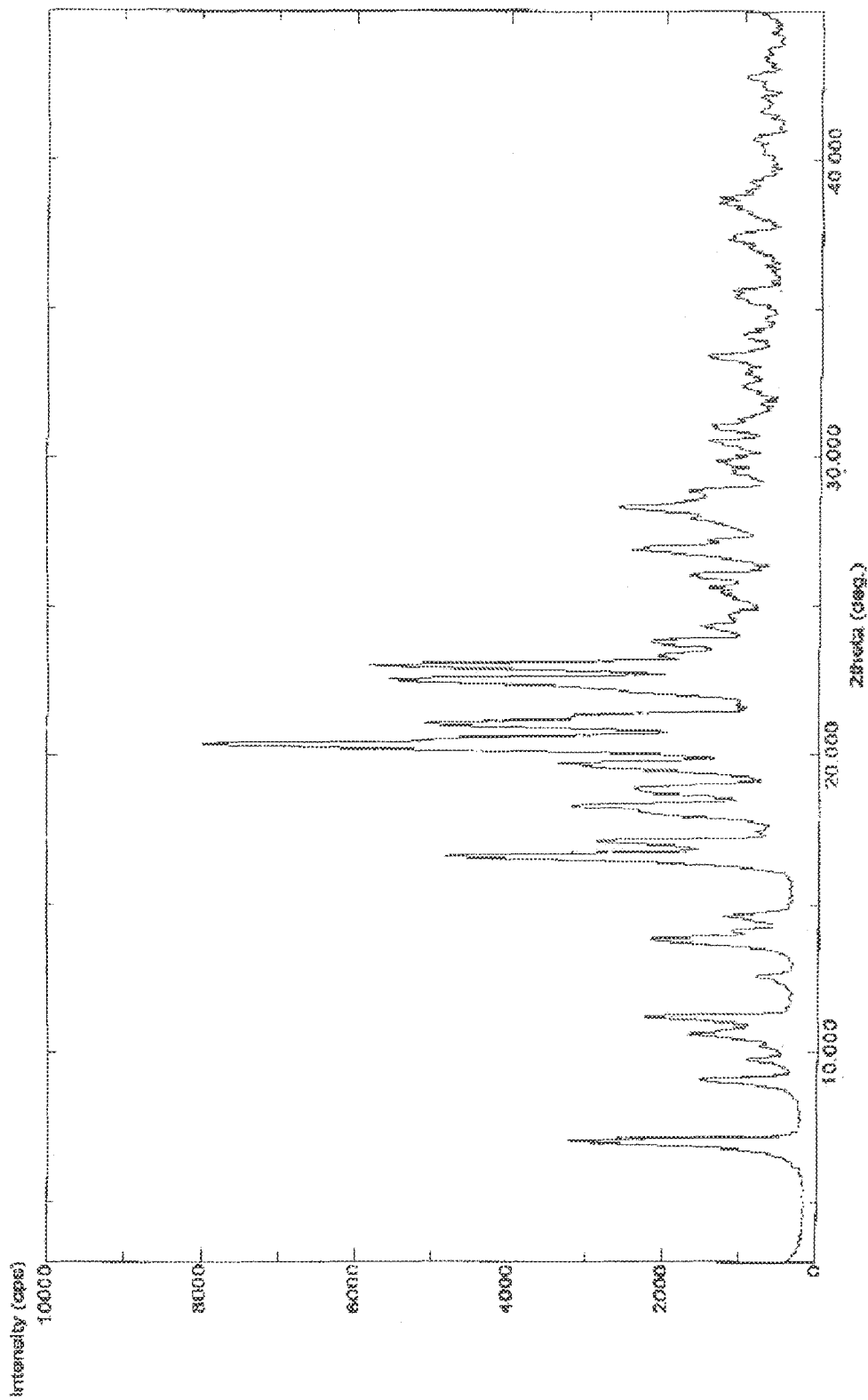
FIG. 1 is the characteristic powder X-ray diffraction (XRD) pattern of darunavir propionate.

The present invention encompasses a process for the preparation of darunavir or solvates or a pharmaceutically acceptable salt thereof with high product yield and quality and substantially free of bisfuranyl impurities. In particular, the present invention provides a process to prepare darunavir, wherein the process excludes the use of multiple solvents and harsh nitro reduction step thereby process more convenient, economical and safe to use on an industrial scale.

In one embodiment, the present invention provides a process for preparation of darunavir of Formula I or a solvate or a pharmaceutically acceptable salt thereof;

Formula I

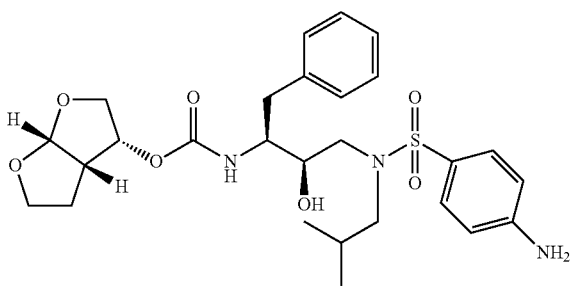

comprising:
a) reacting a compound of Formula IV

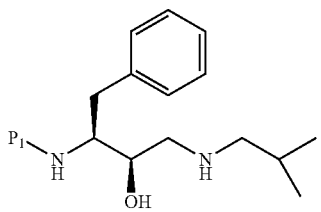
Formula IV wherein 'P₁' represents hydrogen or a suitable amine protecting group, with a protected benzene sulfonyl chloride of Formula IV'

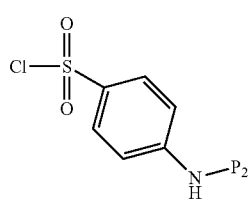
Formula IV' wherein 'P₂' represents hydrogen or a suitable amine protecting group; to obtain a compound of Formula III

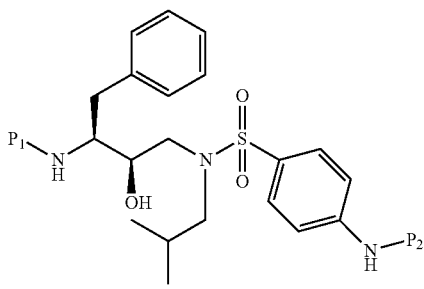
Formula III wherein 'P₁' and 'P₂' represents hydrogen or a suitable amine protecting group,
a) deprotecting the resultant compound with a suitable deprotecting medium to obtain 4-amino-N-(2R, 3S) (3-amino-2-hydroxy-4-phenylbutyl)-N-isobutyl-benzenesulfonamide of Formula II Formula II

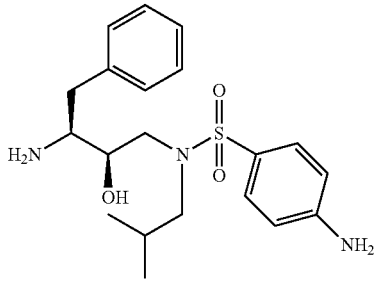

b) reacting the resultant compound of Formula II with (3R, 3aS, 6aR)-hexahydrofuro [2,3-b]furan-3-ol derivative in a mixture of water immiscible organic solvent and water, and
c) isolating darunavir.

As used herein, the term "suitable amino protecting group" refers to a moiety that can be selectively attached to and removed from a nitrogen atom to prevent it from participating in undesired chemical reactions, without unacceptably adverse affects on desired reactions. Examples of amino protecting groups include, but are not limited to acetyl, tertiary butyloxy carbonyl (Boc), p-nitrobenzoyl (PNB), p-methoxybenzoyl (PMB), trityl and the like.

In a preferred embodiment, the suitable amine protecting group 'P₁' represents tertiary butyloxy carbonyl (Boc) and 'P₂' represents acetyl group.

The starting material, a compound of Formula IV, when $P_1$ represents tertiary butyloxy carbonyl, is known in the art and can be prepared by any known method, for example starting Formula IV may be synthesized as disclosed in U.S. Pat. No. 7,772,411.

The reaction of compound of Formula IV, wherein $P_1$ represents tertiary butyloxy carbonyl with protected benzene sulfonyl chloride of Formula IV', wherein $P_2$ represents acetyl group, carried out in an organic solvent in presence of a base to obtain a compound of Formula III.

The organic solvent includes, but is not limited to halogenated hydrocarbons, aromatic hydrocarbons, ethers, amides, nitriles and the like and mixtures thereof. The halogenated hydrocarbons include, but are not limited to methylene chloride, ethylene chloride, chloroform, carbon tertrachloride and the like and mixtures thereof; aromatic hydrocarbons include, but are not limited to toluene, xylene, chlorobenzene and the like and mixtures thereof; ethers include, but are not limited to dimethyl ether, diethyl ether, methyl ethyl ether, diisopropyl ether, methyl tertiary butyl ether, tetrahydrofuran, 1,4-dioxane and the like and mixtures thereof; amides include, but are not limited to dimethyl formamide, dimethyl acetamide, N-methyl pyrrolidinone, hexamethyl phosphoramide and the like and mixtures thereof; nitriles include, but are not limited to acetonitrile, propionitrile and the like and mixtures thereof; preferably methylene chloride, toluene; more preferably methylene chloride.

The base includes, but are not limited to sodium hydroxide, potassium hydroxide, lithium hydroxide, sodium carbonate, potassium carbonate, lithium carbonate, sodium bicarbonate, potassium bicarbonate, ammonia, methyl amine, ethyl amine, dimethylamine, diethylamine, triethylamine N,N-diisopropyl ethyl amine, N,N-dimethylaniline, N,N-dimethyl aminopyridine and the like and mixtures thereof; preferably sodium bicarbonate.

According to step b) of the foregoing process, the deprotection of the compound of Formula III is carried out with a suitable deprotecting medium. The suitable deprotecting medium may be includes by treatment with an acid in an organic solvent to obtain compound of Formula II.

The acid includes, but are not limited to hydrochloric acid, hydrobromic acid, sulfuric acid, perchloric acid, phosphoric acid, acetic acid, trifluoro acetic acid, trichloro acetic acid, methane sulfonic acid and the like and mixtures thereof, preferably hydrochloric acid or sulfuric acid.

The organic solvent for step b) includes, but are not limited to lower alcohols such as methanol, ethanol, isopropanol, n-propanol, n-butanol, isobutanol and the like; nitriles such as acetonitrile, propionitrile and the like; ethers such as tetrhydrofuran, 1,4-dioxane and the like; amides such as dimethyl formamide, dimethyl acetamide and the like; water and mixtures thereof, preferably methanol, acetonitrile, dimethyl formamide; more preferably methanol.

The reaction temperature should be sufficient to effect deprotection reaction. Typically the reaction temperature may be from about ambient temperature to about reflux temperature. The reaction may take from about 2 hours to about 12 hours depending upon the acid, solvent and temperature chosen, preferably about 2 to 4 hours. Preferably the reaction completion at a temperature of about 40° C. to 45° C. for a period of about 8 hours.

In another embodiment, the present invention provides a process for preparation of darunavir or a solvate or a pharmaceutically acceptable salt thereof, comprising reacting 4-amino-N-(2R, 3S) (3-amino-2-hydroxy-4-phenylbutyl)-N-isobutyl-benzenesulfonamide of Formula II with (3R, 3aS, 6aR)-hexahydrofuro [2,3-b]furan-3-ol derivative in a mixture of water immiscible organic solvent and water.

The compound of Formula II may be taken either as a starting material or as an intermediate prepared by the process described above.

Reported literature for coupling reaction of compound of Formula II with (3R, 3aS, 6aR)-hexahydrofuro [2,3-b]furan-3-ol derivative involves multiple solvents and bases, for example process disclosed in the '411 patent involves use of ethyl acetate, acetonitrile and in presence of triethyl amine and methyl amine in ethanol for the coupling reaction, which is disadvantageous for both economic and environmental reasons.

In contrast to the use of multiple solvents and bases the present inventors have now found a procedure in which the reaction is conducted in a mixture of water immiscible organic solvent and water without using any base which provides significant advantages over the former methods. The inventors of the present invention have surprisingly found that the use of certain solvent system enables the formation of darunavir with substantially lower levels of bisfuranyl impurities.

The (3R, 3aS, 6aR)-hexahydrofuro [2,3-b]furan-3-ol is advantageously an activated derivative of hexahydrofuro[2,3-b]furan-3-ol of Formula V:

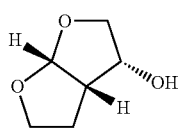

Formula V

The compound of formula (V) above can be prepared in conventional manner for example as described in WO 03/022853, US 2004/0162340, WO 2004/033462, U.S. Pat. No. 6,867,321, WO-2005/095410 and also Ghosh et al, J. Org. Chem. 2004, 69, 7822-7829.

The compound of formula (V) is suitably activated with a coupling agent to generate a hexahydrofuro[2,3-b]furan-3-yl derivative which is then reacted with the compound of formula (II) to obtain the darunavir.

Examples of coupling agents used in reactions are carbonates such as bis-(4-nitrophenyl)carbonate, disuccinimidyl carbonate (DSC), carbonyl diimidazole (CDI). Other coupling agents include chloroformates, such as p-nitrophenylchloroformate, phosgenes such as phosgene, diphosgene and triphosgene.

In particular, when (3R,3aS,6aR)-hexahydrofuro[2,3-b]furan-3-ol is reacted with disuccinimidyl carbonate, 1-([[(3R,3aS,6aR)hexahydrofuro[2,3-b]furan-3-yloxy]-carbonyl]oxy)-2,5-pyrrolidinedione of Formula V' is obtained and is preferred (3R, 3aS, 6aR)-hexahydrofuro [2,3-b]furan-3-ol derivative.

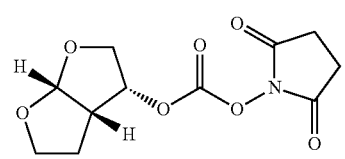

Formula V'

The water immiscible organic solvent includes, but is not limited to esters, ethers, halogenated hydrocarbons, aromatic hydrocarbons and the like. The esters include, but are not limited to methyl acetate, ethyl acetate, isopropyl acetate and the like; ethers include, but are not limited to diethyl ether, methyl tertiary butyl ether and the like; halogenated hydrocarbons include, but are not limited to methylene chloride, ethylene chloride, chloroform, carbon tertrachloride and the like; aromatic hydrocarbons include, but are not limited to toluene, xylene, chlorobenzene and the like; and mixtures thereof, preferably ethyl acetate, methyl tertiary butyl ether, methylene chloride, toluene and the like; more preferably ethyl acetate.

The reaction of compound of Formula II with (3R, 3aS, 6aR)-hexahydrofuro [2,3-b]furan-3-ol derivativeis carried out at a suitable temperature. Typically the reaction temperature may be from about −10° C. to about 60° C. for a period of about 30 minutes to about 8 hours. Preferably the reaction temperature is about room 20° C. to about 30° C. for a period of about 2 hours to 5 hours.

After completion of the reaction, the reaction mass can be treated with an aqueous base solution, wherein the base is selected from any base known in the art, for example sodium hydroxide, potassium hydroxide, sodium carbonate, potassium carbonate and the like; and isolating the darunavir by any method known in the art, for example by solvent evaporation to obtain crude darunavir.

In another embodiment, the present invention provides a process for preparation of darunavir in crystalline form, comprising a) treating any form of darunavir or crude darunavir obtained just above with a carboxylic acid solvent and b) isolating the darunavir in crystalline form.

The carboxylic acid solvent used in step a) includes, but is not limited to propionic acid.

Step a) of treating the darunavir with a carboxylic acid solvent further comprising the steps of: dissolving darunavir in a carboxylic acid solvent. The solvent may be heated to obtain a solution at a temperature of from about ambient temperature to about reflux temperature. The reaction solution may be cooled at a temperature from about 30° C. or less such that the darunavir can be isolated by conventional techniques, for example filtration.

Darunavir recovered using the process of crystallization from a carboxylic acid solvent; preferably propionic acid of the invention is solvate form of darunavir, preferably darunavir propionate solvate.

In another embodiment, the present invention provides darunavir propionate solvate.

In a further embodiment, the present invention provides characterization via X-ray powder diffraction pattern of a darunavir propionate solvate, which is substantially in accordance with FIG. 1. The X-Ray powder diffraction can be measured by an X-ray powder Diffractometer equipped with a Cu-anode ([λ]=1.54 Angstrom), X-ray source operated at 30 kV, 15 mA and a Ni filter is used to strip K-beta radiation. Two-theta calibration is performed using an NIST SRM 640c Si standard. The sample was analyzed using the following instrument parameters: measuring range=3-45°2θ; step width=0.020°; and scan speed=2°/minute.

In another embodiment, the darunavir propionate solvate of the invention can be used as intermediate or as starting material for the preparation of darunavir in amorphous form.

In a further embodiment, the present invention provides a process for preparation of amorphous darunavir, comprising:
  a) providing a solution of darunavir in any form or obtained by the processes herein described above in an acid and water,
  b) combining step a) solution and a solution of a base and water,
  c) recovering amorphous darunavir.

In a further embodiment, the present invention provides a process for preparation of amorphous darunavir, comprising:
  a) providing a solution of darunavir or a solvate thereof, obtained by the processes herein described above in an acid and a solvent optionally a base,
  b) combining step a) solution and a solution of a base and water,
  c) recovering amorphous darunavir.

Any form of darunavir can be used as starting material in the process of making the amorphous darunavir of the present invention.

Ideally, darunavir propionate solvate, obtained by the processes herein described previously, is the starting material in the process of making the amorphous darunavir.

Useful acids for carrying out the process for the preparation of amorphous darunavir of the invention include carboxylic acid. The carboxylic acid include, but are not limited to acetic acid, propionic acid, formic acid, trifluoroacetic acid, butanoic acid, pentanoic acid, hexanoic acid, heptanoic acid and the like and mixtures thereof; preferably acetic acid.

The optional base used in step a) is selected from any base known in the art, for example the base include, but are not limited to ammonia, sodium carbonate, potassium carbonate, sodium bicarbonate, potassium bicarbonate, cesium carbonate and the like and mixtures thereof, preferably ammonia.

The solvent used herein for step a) includes, but are not limited to nitriles such as acetonitrile, propionitrile and the like; alcohols such as methanol, ethanol, isopropanol and the like; water and mixtures thereof, preferably acetonitrile or a mixture of acetonitrile and water.

The base used for step b) is any base known in the art, for example the base used for optional step a) is used for step b).

The temperature for the preparation of solution in a) of the process can range from about −20° C. to about 85° C.; preferably about 20° C. to about 40° C.

Preferably, the step a) of the process for preparation of amorphous darunavir consists of mixing darunavir propionate solvate in a mixture of acetonitrile and acetic acid and then with ammonia to obtain a clear solution, which is proceed for step b).

Combining step a) solution and a solution of a base and water can be carried out in any known manner, for example step a) solution is added to a solution of base and water or the solution of base and water is added to a solution of step a).

The temperature suitable for combining step a) solution and a solution of base and water of step b) may be at about −20° C. to about 40° C.; preferably −10° C. to about 0° C.

The amorphous darunavir can be recovered by any conventional techniques known in the art, for example filtration. Typically, if stirring is involved, the temperature during stirring can range from about −10° C. to about 30° C. The resultant product may optionally be further dried by techniques known in the art, for example tray drying under vacuum.

The present invention advantageously provides darunavir or a solvate or a pharmaceutically acceptable salt thereof, obtained by the process described herein, having a chemical purity of at least about 98%, as measured by HPLC, preferably at least about 99%, as measured by HPLC, and more preferably at least about 99.8%, as measured by HPLC; substantially free of one or more impurities as described in Table 1:

Impurity A

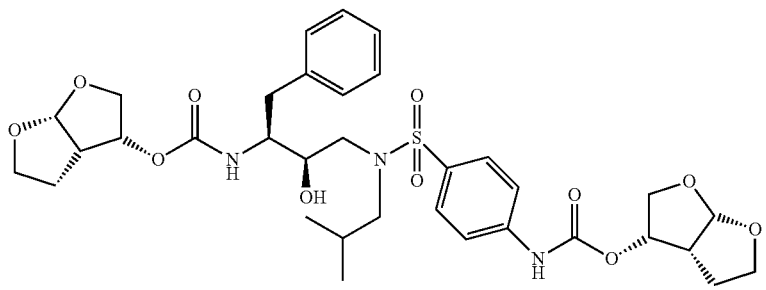

Impurity B
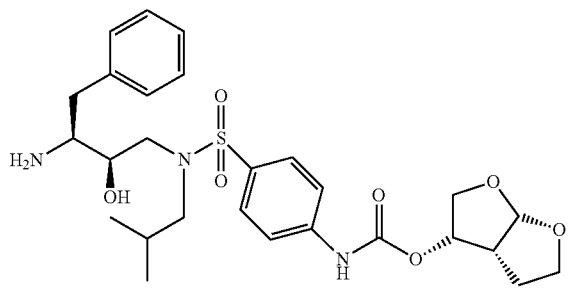
Impurity C
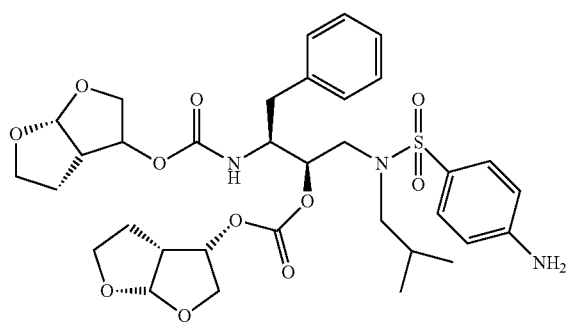
Impurity D
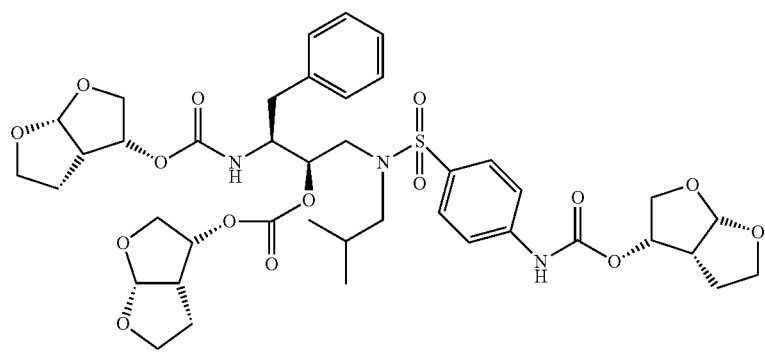
Formula II
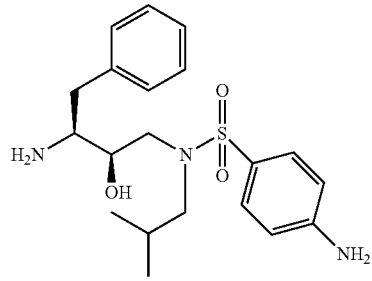 [SMILES: CC(C)CN(C[C@@H](O)[C@@H](N)Cc1ccccc1)S(=O)(=O)c1ccc(N)cc1]
Isocyanate Impurity
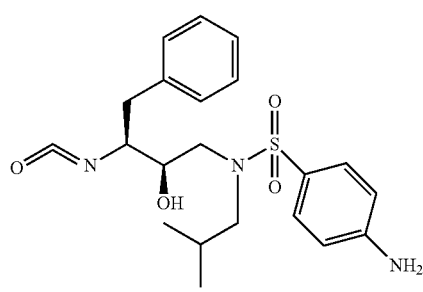 [SMILES: CC(C)CN(C[C@@H](O)[C@H](Cc1ccccc1)N=C=O)S(=O)(=O)c1ccc(N)cc1]

N-Acetyl Danunavir

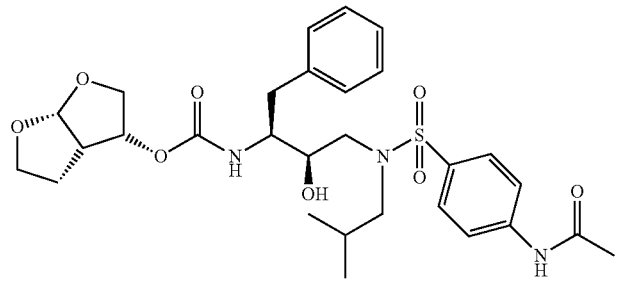

(R,S)-diastereomer

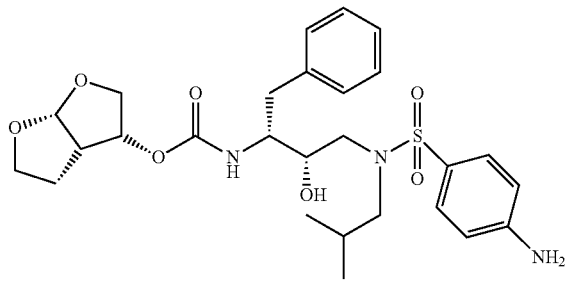

(S,S)-diastereomer

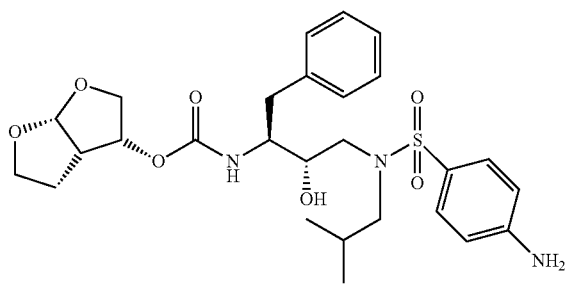

(R,R)-diastereomer

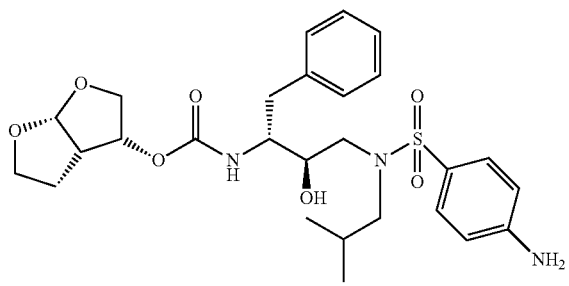

wherein the word "substantially free" refers to darunavir or a solvate or a pharmaceutically acceptable salt thereof having less than about 0.1%, preferably less than 0.05% of Impurity A or Impurity B or Impurity C or Impurity D or Formula II or Isocyanate Impurity or N-Acetyl Darunavir or (R,S)-diastereomer or (S,S)-diastereomer or (R,R)-diastereomer, as measured by HPLC.

The reported literature for instance the '411 patent, '322 publication and the '604 publication discloses process for the preparation of darunavir, which was involved either use of multiple solvents and base during the reaction of amine compound of Formula II and (3R,3aS,6aR)-hexahydrofuro[2,3-b]furan-3-ol derivative or involving harsh nitro reduction steps, results darunavir contain high levels of bisfuranyl impurities i.e. Impurity A, Impurity B or Impurity C or process related impurities i.e. Isocyanate Impurity or N-acetyl darunavir. In contrast, the process herein described arrives at a darunavir, which may be involved an improved process conditions such as mixture of simple water immiscible organic solvent and water instead of multiple solvents and base and avoids nitro reduction step. Particularly, the process herein described allows that a darunavir may be prepared substantially lower level of above mentioned impurities.

The present invention provides darunaviror solvates or a pharmaceutically acceptable salt thereof, obtained by the above process, as analyzed using the high performance liquid chromatography ("HPLC") with the conditions described below:

Column: Symmetry shield, RP-18, 5 µm

Column temperature: 30° C.

Diluent: Water:Acetonitrile (1:1)

Flow rate: 1.0 mL/min

Detection wavelength: 215 nm

Injection volume: 10 µL

Mobile Phase:
a) Buffer:Acetonitrile (9:1)
b) Buffer:Acetonitrile (3:7)
Buffer:Potassium dihydrogen phosphate in water at pH to 3.0 with o-phosphoric acid.
Gradient Program:

| Time (Min) | Mobile phase A % (v/v) | Mobile phase B % (v/v) |
|---|---|---|
| 0 | 70 | 30 |
| 5 | 70 | 30 |
| 30 | 25 | 75 |
| 40 | 10 | 90 |
| 60 | 10 | 90 |
| 65 | 70 | 30 |
| 75 | 70 | 30 |

The present invention provides darunavir in amorphous form, obtained by the process disclosed herein, is characterized by an average size of about 40 μm for 50% of the particles, about 20 μm for 10% of the particles and about 100 μm for 90% of the particles. The present invention further provides amorphous darunavir, obtained by the process disclosed herein, is characterized by an average size of less than about 40 μm for 50% of the particles, less than about 15 μm for 10% of the particles and less than about 90 μm for 90% of the particles, obtained upon milling.

Micronization is carried out by methods known in art such as jet milling, media milling, pulverization and the like. The particle size of the amorphous darunavir obtained by the process of the invention can be determined by any method known in the art such as laser diffraction, sieve analysis, microscope observation, sedimentation and the like. The particle size measurement employed Malvern Mastersizer-2000, equipped with Malvern hydro2000S (A) sample handling unit.

The present invention provides darunavir in amorphous form, obtained by the process disclosed herein, is characterized by having bulk density of particles of about 0.5 g/ml. The present invention further provides amorphous darunavir, obtained by the process disclosed herein, is characterized by having bulk density of particles of about 0.4 g/ml.

The bulk density used tapped density tester dual-platform ETD-1020 (Electrolab). System specifications: Speed: nominal rate of 300 taps per minute, Accuracy: Actual setting±1 tap, Drop height: 14±2 mm. Platform rotation: 5-15 rotations/minute.

Another embodiment of the present invention is directed to a pharmaceutical composition containing at least the substantially pure darunavir or a solvate or a pharmaceutically acceptable salt thereof, particularly amorphous darunavir disclosed herein and at least one pharmaceutically acceptable excipient. Such pharmaceutical composition may be administered to a mammalian patient in any dosage form, e.g., liquid, powder, elixir, injectable solution, etc.

The present invention has the following advantages with respect to the reported literature, are:
a) It involves simple water immiscible organic solvent and water during the reaction of amine compound of Formula II and (3R,3aS,6aR)-hexahydrofuro[2,3-b]furan-3-ol derivative, which avoids formation of bisfuranyl impurities,
b) The process of the present invention herein described is convenient and scalable as it carried out at room temperature during the furanyl ester formation and addition of (3R,3aS,6aR)-hexahydrofuro[2,3-b]furan-3-ol derivative in a instantaneous instead of addition in prolonged period of time,
c) It avoids harsh nitro reductions using palladium with hydrogen gas, making the process of more convenient and safe to use on an industrial scale as it avoids decomposition of carbamate linkage,
d) Darunavir prepared by the process of the present invention has improved purity and contain substantially free of unwanted bisfuranyl impurities.

EXAMPLES

The following non limiting examples illustrate specific embodiments of the present invention. They are not intended to be limiting the scope of the present invention in any way.

Example 1

Preparation of 4-amino-N-(2R, 3 S) (3-amino-2-hydroxy-4-phenylbutyl)-N-isobutyl-benzenesulfonamide of Formula II A 3 L round bottom flask fitted with a mechanical stirrer, thermometer socket, addition funnel was charged (1-benzyl-2-hydroxy-3-isobutylaminopropyl) carbamic acid tertiary butyl ester of Formula IV (100 gms) and MDC (1500 ml). The reaction temperature was stirred for 10 minutes at 20° C. to 30° C. and to the resultant solution sodium bicarbonate (37.5 gms) and water (300 ml) was added. N-(Acetylamino) benzenesulfonyl chloride was charged in equal lots (4×19.1 gms) at about 25-30° C. The reaction was stirred at about 25°-35° C. for about 2 hours and the reaction completion was monitored by HPLC. After completion of the reaction, the layers were separated and organic layer was washed with ammonia solution (200 ml) and then with aq HCl solution (9 ml of con. HCl+300 ml water). The layers were separated and the MDC was distilled off completely to obtain residue. To the residue, methanol (300 ml) and dil. sulfuric acid (145.6 gms of sulfuric acid+27 ml water) was added and the reaction temperature was raised to 40° C. to 45° C. and maintained for about 8 hours and the reaction completion was monitored by HPLC. After completion of the deprotection, water (1000 ml) and toluene (50 ml) was charged and layers were separated. To the product containing aqueous layer, MDC (1200 ml) was charged and allowed to cool to 0-5° C. and adjusted pH to about 12 with aqueous sodium hydroxide. The reaction mass temperature was raised to about 25-30° C., stirred for 10 minutes and the organic layer was separated. The aqueous layer was extracted with MDC (300 ml) and separated. The total organic layer was washed with water (2×300 ml) and the MDC was distilled completely under vacuum at below 40° C. and the obtained residue was dissolved in ethyl acetate (500 ml) and methanol (40 ml) and stirred for 30 mins at 35-40° C. The reaction solution was allowed to cool to 0° C. to 5° C. and stirred for about 60 minutes at same temperature. Precipitated solid was filtered and washed with chilled ethyl acetate (50 ml). The wet product was dried at about 50° C. to about 55° C. under reduced pressure to provide the title compound.

Yield: 101 gms.
HPLC purity: 99.2%

Example 2

Preparation of 4-amino-N-(2R, 3 S) (3-amino-2-hydroxy-4-phenylbutyl)-N-isobutyl-benzenesulfonamide of Formula II A 3 L round bottom flask fitted with a mechanical stirrer, thermometer socket, addition funnel was charged (1-benzyl-2-hydroxy-3-isobutylaminopropyl) carbamic acid tertiary butyl ester of Formula IV (100 gms) and MDC (2000 ml). The reaction temperature was stirred for 10 minutes at 20° C. to 30° C. and N-(Acetylamino) benzene sulfonyl chloride (79.8 gms) was charged. The reaction mixture was allowed to cool to 10° C. and aqueous sodium bicarbonate solution (1000 ml) was added. The reaction temperature was raised to 25° C. to 30° C. and maintained for about 1 hour. The layers were separated and organic layer was washed with ammonia solution (100 ml) and then with DM water (500 ml). The layers were separated and the MDC was distilled off completely to obtain residue. To the residue, methanol (800 ml) and CP. HCl (125 ml) was charged and the reaction temperature was raised to 60° C. to 65° C. and maintained for 4 hours. Methanol was distilled completely under vacuum at below 60° C. and the obtained residue was charged water (2200 ml) and ethyl acetate (2200 ml). The reaction mass pH was adjusted to about 9 with aqueous sodium hydroxide solution and layers were separated. The organic layer was washed with water and the ethyl acetate was distilled under vacuum below 40° C. up to minimum volume remains in the flask. The reaction solution was allowed to cool to 20° C. to 30° C. and stirred for about 60 minutes and further allowed to cool to 0° C. to 5° C. Precipitated solid was filtered and washed with ethyl acetate (100 ml). The wet product was dried at about 50° C. to about 55° C. under reduced pressure to provide the title compound.
Yield: 102 gms.
HPLC purity: 99%

Example 3

Preparation of Darunavir Propionate Solvate

A 2 L round bottom flask fitted with a mechanical stirrer, thermometer socket, addition funnel was charged 1-([[(3R, 3aS,6aR)hexahydrofuro[2,3-b]furan-3-yloxy]-carbonyl]oxy)-2,5-pyrrolidinedione of Formula V (65.6 gms), ethyl acetate (1000 ml) and water (200 ml) at 25° C. to 30° C. To the reaction mass Formula II (100 gms; obtained from Example 1) was added at 25° C. to 30° C. and stirred for about 90-120 minutes at same temperature and the reaction completion was monitored by HPLC. After completion of the reaction, the organic layer and the aqueous layers were separated and the organic layer was washed with 5% aqueous sodium bisulfate solution (2×300 ml; 15 gms of sodium bisulfate+285 ml water) followed by with 10% aqueous potassium carbonate solution (300 ml) and then with water (300 ml) and aqueous sodium chloride solution (300 ml). Aqueous and organic layers were separated and the organic layer was distilled off completely under vacuum at below 40° C. to obtain residue. To the residue, ethyl acetate (25 ml) and propionic acid (1000 ml) was added at temperature 15-20° C. and stirred for about 30 mins at same temperature. The reaction mass was allowed to cool to 0-5° C. and stirred for about 90 mins. Precipitated solid was filtered and washed with chilled propionic acid (50 ml). The wet product was dried at about 45° C. to about 50° C. under reduced pressure to provide the title compound.
Yield: 135 gms.
HPLC purity: 99.3%
Formula II: 0.05%
The XRPD is set forth in FIG. 01

Example 4

Preparation of Darunavir Propionate Solvate

A 2 L round bottom flask fitted with a mechanical stirrer, thermometer socket, addition funnel was charged 1-([[(3R, 3aS,6aR)hexahydrofuro[2,3-b]furan-3-yloxy]-carbonyl]oxy)-2,5-pyrrolidinedione of Formula V (68 gms), ethyl acetate (1500 ml) and water (200 ml) at 25° C. to 30° C. To the reaction mass added Formula II (100 gins) at 25° C. to 30° C. and stirred for 60 minutes at same temperature. To the reaction mass charged 10% aqueous potassium carbonate (500 ml) and layers were separated and the organic layer was washed with DM water (500 ml). The layers were separated and the ethyl acetate was distilled off completely under vacuum to obtain residue (Darunavir: 97.1%, Formula II: 2%, Impurity A: less than 0.10%, Impurity C: less than 0.05%). To the residue, charged propionic acid (1000 ml) and stirred for 60 minutes at 25° C. to 30° C. Precipitated solid was filtered and washed with propionic acid (100 ml) followed by diisopropyl ether (200 ml). The wet product was dried at about 60° C. to about 70° C. under reduced pressure to provide the title compound.
Yield: 125 gms.
HPLC purity: 99.5%,
Formula II: 0.06%
The XRPD is set forth in FIG. 01
Experimental Data:
The impurity profile as measured by high performance liquid chromatography for three batches of darunavir propionate solvate of the present invention is set forth below in Table II.

TABLE II

| Batch | Impurity A | Impurity B | Impurity C | Impurity D |
|---|---|---|---|---|
| 1 | 0.02% | ND | 0.01% | ND |
| 2 | 0.05% | ND | 0.03% | ND |
| 3 | 0.04% | ND | 0.02% | ND |

ND: Not detected

Example 5

Preparation of darunavir as procedure analogous to that employed in Example 3, using mixture of different water immiscible solvent and water as described in the following Table III:

TABLE III

| S. No | Formula II (Example 1) | Formula V | Water immiscible Solvent | Purity |
|---|---|---|---|---|
| 01 | 0.5 gms | 0.36 gms | MDC + water | Darunavir: 95.3%; Formula II: 1.66% |
| 02 | 0.5 gms | 0.36 gms | Toluene + water | Darunavir: 99.58% Formula II: 1.82% |

Example 6

Preparation of Amorphous Darunavir

A 3 L round bottom flask fitted with a mechanical stirrer, thermometer socket, addition funnel was charged acetic acid (300 ml) and Acetonitrile (75 ml) at 25° C. to 30° C. The mass was allowed to cool to 5-10° C. and darunavir propionate solvate (100 gms; obtained from Example 3) was charged at same temperature. To the reaction mass, con. Ammonia solution (25 ml) was added at same temperature and the solution was allowed to cool to 0° C. to 5° C. and kept aside.

In another round bottom flask charged water (2000 ml) and ammonia (800 ml) and allowed to cool to −10° C. to −5° C. To this solution, darunavir propionate solution was added at a temperature of −10° C. to −5° C. and stirred for 30 minutes at same temperature. The reaction mass temperature was raised to about 15° C. and stirred for about 60 mins at same temperature. Precipitated solid was filtered and washed with water (1000 ml). The wet product was slurred in water (2500 ml), filtered and washed with water (1000 ml). The wet product was dried at about 45° C. to about 50° C. under reduced pressure to provide the title compound.

Yield: 77 Gms.

HPLC purity: 99.7%

| | | | |
|---|---|---|---|
| Impurity A | 0.03% | Isocyanate Impurity | 0.01% |
| Impurity B | Not Detected | N-Acetyl Darunavir | 0.03% |
| Impurity C | 0.04% | (R,S)-diastereomer | 0.03% |
| Impurity D | Not Detected | (S,S)-diastereomer | BDL |
| Diamine | 0.01% | (R,R)-diastereomer | BDL |

LOD: 0.006%

The XRPD is set forth in FIG. 02

Example 7

Preparation of Amorphous Darunavir

A 3 L round bottom flask fitted with a mechanical stirrer, thermometer socket, addition funnel was charged water (800 ml) acetic acid (1000 ml) at 25° C. to 30° C. To the solution charged darunavir propionate solvate (100 gms; obtained from Example 2) at 15° C. to 20° C. and stirred for 10 minutes at same temperature. The solution was allowed to cool to 0° C. to 5° C. and kept aside. In another round bottom flask charged water (2000 ml) and ammonia (850 ml) and allowed to cool to 0° C. to 5° C. To the solution of water and ammonia, added darunavir solution at temperature of −5° C. to 0° C. and stirred for 30 minutes at a same temperature. Precipitated solid was filtered and washed with water (1000 ml). The wet product was slurred in water (2000 ml), filtered and washed with water (100 ml). The wet product was dried at about 25° C. to about 35° C. under reduced pressure to provide the title compound.

Yield: 75 Gms.

HPLC purity: 99.7%, Impurity A: 0.02%, Impurity C: 0.03%, Impurity B & Impurity D: Not Detected The XRPD is set forth in FIG. 02

Example 8

Characterization of Isocyanate Impurity and N-Acetyl Darunavir

Isocyanate Impurity

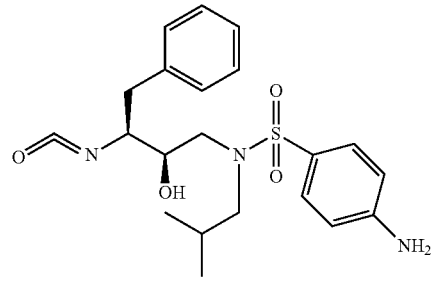 [SMILES: CC(C)CN(C[C@@H](O)[C@H](Cc1ccccc1)N=C=O)S(=O)(=O)c1ccc(N)cc1]

$^1$HNMR (300 MHz, DMSO-d$_6$): δ 7.63 (s, 1H), 7.31 (m, 2H), 7.24 (m, 2H), 7.21 (m, 2H), 7.18 (d, 2H, J = 8.4 Hz), 6.55 (d, 2H, J = 8.1 Hz), 5.98 (s, 2H), 4.69 (m, 1H), 4.22 (q, 1H, J = 7.5 Hz), 3.21 (m, 2H), 2.84 (m, 1H), 2.80 (m, 1H), 2.72 (m, 1H), 2.58 (dd, 1H, J = 13.5, 6.0 Hz), 1.83 (m, 1H), 0.83 (d, 3H, J = 6.3 Hz), 0.77 (d, 3H, J = 6.6 Hz),

Mass: ES-MS m/z 418 (M + H)$^+$, 440 (M + Na)$^+$

N-Acetyl Darunavir

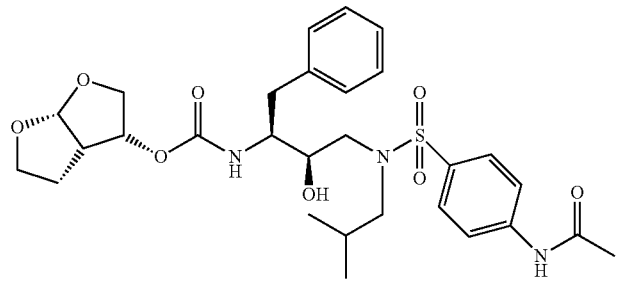

$^1$HNMR (300 MHz, DMSO-d$_6$): δ 11.95 (br, 1H), 10.31 (br, 1H), 7.74 (d, 2H, J = 8.7 Hz), 7.68 (d, 2H, J = 8.7 Hz), 7.20 (m, 2H), 7.19 (m, 2H), 7.11 (m, 1H), 5.49 (d, 1H, J = 5.1 Hz),

-continued 5.04 (d, 1H, J = 6.3 Hz), 4.83 (m, 1H), 3.86 (dd, 1H, J = 9.0, 6.0 Hz), 3.70 (dd, 1H, J = 9.0, 6.0 Hz), 3.59 (m, 1H), 3.58 (m, 1H), 3.57 (m, 1H), 3.53 (m, 1H), 3.31 (m, 1H), 3.01 (m, 1H), 3.00 (m, 1H), 2.75 (m, 2H), 2.72 (m, 1H), 2.44 (m, 1H), 2.06 (m, 1H), 1.95 (m, 1H), 1.35 (m, 1H), 1.20 (m, 1H), 0.83 (d, 3H, J = 6.6 Hz), 0.77 (d, 3H, J = 6.6 Hz)
Mass: ES-MS m/z 590 (M + H)$^+$, 612 (M + Na)$^+$ While the invention has been described with reference to above detailed description and the preferred examples, it is not intended to be limited thereto. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:
1. A process for preparation of amorphous darunavir, comprising the steps of:
   a) providing a first solution comprising an acid and a solvent, at a temperature of about −5° C. to about 10° C., wherein the acid is acetic acid and the solvent is either acetonitrile or water;
   b) adding an amount of darunavir propionate solvate to the first solution to form a second solution;
   c) combining the second solution of step b) with a base and water at a temperature of about −10° C. to about 0° C., wherein the base is ammonia to form a third solution; and
   c) recovering the amorphous darunavir from the third solution of step b), wherein the purity of the amorphous darunavir is equal to or greater than about 99.7% as measured by HPLC.
2. The process of claim 1, wherein the solvent used in the first solution of step a) is acetonitrile.
3. The process of claim 1, wherein the first solution of step a) is provided at a temperature of about 5° C. to about 10° C.
4. The process of claim 1, wherein the third solution formed in step b) is subsequently stirred at a temperature of about −10° C. to about −5° C.
5. The process of claim 1, further comprising forming a pharmaceutical composition by combining the recovered amorphous darunavir with at least one pharmaceutically acceptable excipient.
6. A process for preparation of amorphous darunavir, comprising the steps of:
   a) forming a first solution by dissolving a darunavir solvate in an acid and a solvent at a temperature of about −5° C. to about 10° C., wherein the acid is acetic acid and the solvent is either acetonitrile or water;
   b) combining the first solution with a second solution comprising a base and water at a temperature of about −10° C. to about 0° C. to form a third solution; and
   c) recovering by filtration the amorphous darunavir from the third solution, wherein the purity of the amorphous darunavir is equal to or greater than about 99.7% as measured by HPLC.

7. The process of claim 6, further comprising:
   d) combining the recovered amorphous darunavir with at least one pharmaceutically acceptable excipient for use as a pharmaceutical composition.
8. The process of claim 6, wherein the purified amorphous darunavir includes less than 0.04% as measured by HPLC of any one of:

Impurity A

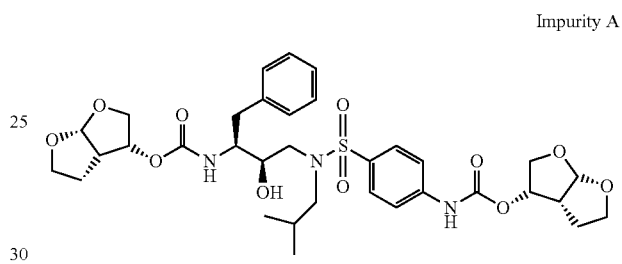

Impurity B

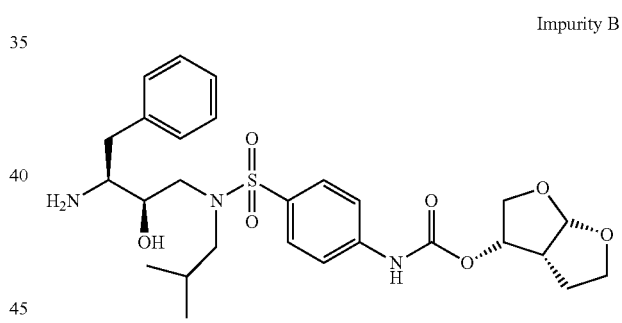

Impurity C

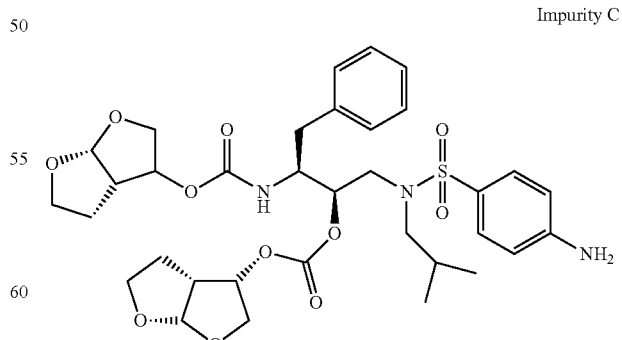

-continued
Impurity D
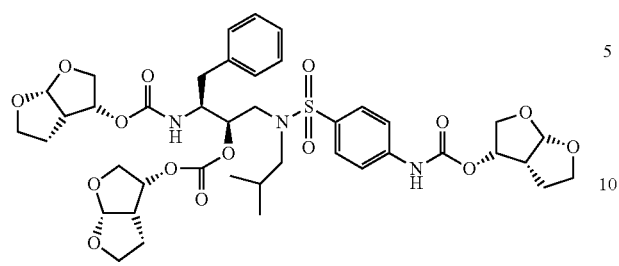
Formula II
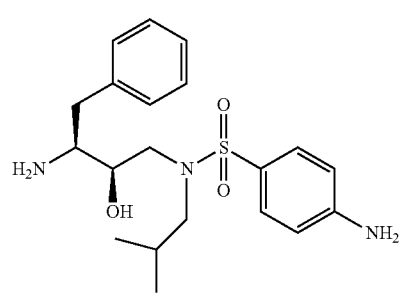
-continued
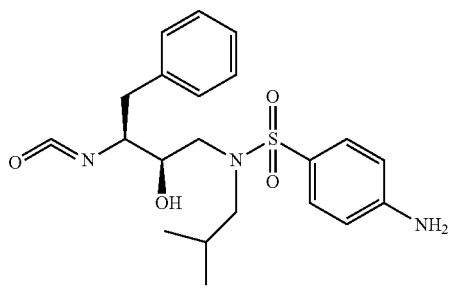
Isocyanate Impurity
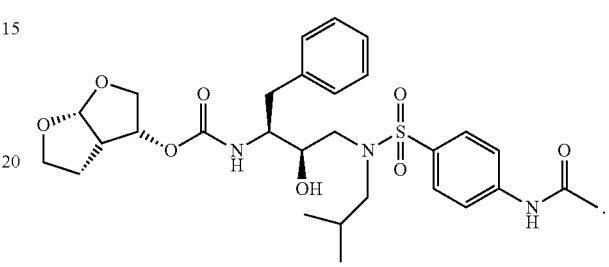
N-Acetyl Darunavir
* * * * *